US006763835B1

(12) United States Patent
Grove et al.

(10) Patent No.: US 6,763,835 B1
(45) Date of Patent: Jul. 20, 2004

(54) CHEMICAL/BIOLOGICAL SPECIAL OPERATIONS MASK

(75) Inventors: Corey M. Grove, Red Lion, PA (US); Stephen E. Chase, Jarrettsville, MD (US); Jeffery S. Hofmann, Abingdon, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 193 days.

(21) Appl. No.: 09/968,193

(22) Filed: Oct. 1, 2001

(51) Int. Cl.[7] .................................................. A61F 11/00

(52) U.S. Cl. ............. 128/857; 128/201.25; 128/205.28; 128/205.29

(58) Field of Search ................................. 128/846, 847, 128/857, 201.25, 201.29, 202.11, 202.19, 205.28, 205.29

(56) References Cited

U.S. PATENT DOCUMENTS 1,041,610 A * 10/1912 Fabian
2,800,901 A * 7/1957 Monro
4,352,353 A * 10/1982 Bolton .................. 128/201.24
5,113,854 A * 5/1992 Dosch .................... 128/201.23
5,263,477 A * 11/1993 Crome .................. 128/205.24
H1316 H * 6/1994 McGuinness .......... 128/201.25
6,158,429 A * 12/2000 Gardner ................. 128/201.25
6,176,239 B1 * 1/2001 Grove .................... 128/206.24
6,340,024 B1 * 1/2002 Brookman ............. 128/201.25

* cited by examiner

*Primary Examiner*—Michael A. Brown
(74) *Attorney, Agent, or Firm*—Ulysses John Biffoni

(57) ABSTRACT

A respiratory mask assembly for filtering airborne biological and/or chemical agents from air for breathing, comprises an outer hood adapted to seal with and encompass at least the head and neck of a wearer from ambient atmosphere, at least one transparent lens attached to the outer hood for providing visual sight to the wearer, at least one filter assembly attached to the outer hood, the filter assembly adapted for filtering airborne biological and/or chemical agents from air passing therethrough, an airflow regulator located in the outer hood, the airflow regulator including an outlet adapted for expelling exhaled air to ambient, and an inlet adapted for drawing air thereinto, and air conveying means located in the outer hood for conveying air filtered through the filter assembly from ambient to the inside surface of the transparent lens for drawing into the airflow regulator inlet.

21 Claims, 6 Drawing Sheets

CHEMICAL/BIOLOGICAL SPECIAL OPERATIONS MASK

GOVERNMENTAL INTEREST

The invention described herein may be manufactured, licensed, and used by or for the U.S. Government.

FIELD OF THE INVENTION

The present invention relates generally to respiratory masks, more particularly to full-face respiratory masks adapted for protecting the wearer against biologically/chemically hazardous materials especially in the form of airborne particulates, vapors and aerosols.

BACKGROUND OF THE INVENTION

Respiratory masks that are adapted to protect the wearer's face, eyes, and lungs from the effects of hazardous airborne particles of a chemical or biological nature were first used to protect soldiers during war against poison gases. Today such masks have evolved and developed for use in many capacities, including, but not limited to firefighting, environmental cleanup, manufacturing, medical hazard handling, quarantining of patients with highly contagious pathogens, biological and chemical warfare, mining, paint applications, construction, and other applications where persons may come into contact with hazardous substances especially those of airborne nature.

Typically, the mask is worn over the wearer's face sealed from the ambient atmosphere and cleans the air entering the mask by means of a filter device generally comprised of chemically impregnated fibers or a bed of adsorbent material usually activated charcoal. During operation, a one-way inlet valve in the mask allows air drawn in by the wearer's lungs into a filter containing the absorbent material, whereby the filtered air then flows into the mask. Thus, the air is filtered and cleaned as it enters the mask. As the wearer exhales, the exhaled gas is expelled through a one-way exit valve out of the mask and the process is repeated with each breath.

Full-face respiratory masks are typically uncomfortable and difficult to wear for long periods of time and impose significant burden on the wearer. Such masks are typically heavy and bulky, restrict vision, generate heat stress and discomfort for the wearer, difficult to breathe through, and trap moisture vapors and perspiration causing lens fogging and discomfort. In addition, when the masks are not worn, they are cumbersome to carry and often cannot be folded without damage into a compact form.

For the foregoing reasons, there is a need for a full-face respiratory mask useful for protecting the wearer against hazardous chemical and biological agents in the form of aerosols, vapors and the like, while maintaining long-term wearability, improved long-term chemical and biological protection, and capacity to be packed into a small compact package. The full-face respiratory mask of the present invention as described herein overcomes the shortcomings described above.

SUMMARY OF THE INVENTION

The present invention provides a respiratory mask assembly for protecting a wearer from biological and/or chemical agents that may be present in an atmosphere. The respiratory mask of the present invention provides a military level of protection against biological and chemical agents over a long period of time without similar level of burden and discomfort often associated with full-face mask configurations. The respiratory mask is configured to be highly compact and portable so that it may be conveniently carried and/or packed into a tightly compact hermetically sealed package prior to wear. The mask is easily manufactured using inexpensive and readily available component parts and equipment. In addition, the design of the mask provides the wearer a wide unobstructed field of vision while allowing the wearer to effectively communicate with others. The mask is further adapted to minimize moisture-related fogging and accumulation of carbon dioxide in the interior thereof and facilitate the dissipation of heat and perspiration unavoidably generated by the wearer, while providing a high level of chemical/biological protection suitable especially for military use.

In one aspect of the present invention there is provided a respiratory mask assembly for filtering airborne biological and/or chemical agents from air for breathing, which comprises:

- an outer hood adapted to seal with and encompass at least the head and neck of a wearer from ambient atmosphere;
- at least one transparent lens attached to the outer hood for providing visual sight to the wearer;
- at least one filter assembly attached to the outer hood, the filter assembly adapted for filtering airborne biological and/or chemical agents from air passing therethrough;
- an airflow regulator located in the outer hood, the airflow regulator including an outlet adapted for expelling exhaled air to ambient, and an inlet adapted for drawing air thereinto; and
- air conveying means located in the outer hood for conveying air filtered through the filter assembly from ambient to the inside surface of the transparent lens for drawing into the airflow regulator inlet.

BRIEF DESCRIPTION OF THE DRAWINGS

Various embodiments of the invention are described in detail below with reference to the drawings, in which like items are identified by the same reference designation, wherein.

DETAILED DESCRIPTION OF THE INVENTION

The present invention is directed to respiratory masks adapted for filtering biologically/chemically hazardous particulates, aerosols and the like from ambient air for providing safe breathable life sustaining air to the wearer. The respiratory mask of the present invention provides the wearer with suitable protection against biological and chemical atmospheric fallout while minimizing the limitations and problems associated with conventional full-face respiratory masks. The respiratory mask of the present invention is designed to possess low bulk and weight for increased wear comfort, and may be packaged in a compact form for easy portability. In addition, the respiratory mask is simple and inexpensive to manufacture while providing the high level of protection especially suitable for military use.

The present invention is generally directed to a respiratory mask that includes means contained therein for conveying to the wearer's mouth and/or nose, ambient air filtered through a filter medium located on hood of the mask. The air conveying means and the mask is further adapted, in combination, to remove or wick moisture away from the wearer's skin enclosed thereunder, thus reducing the discomfort associated with heat stress and moisture retainment, while preventing the penetration of harmful aerosols and particulates to the wearer.

Figure 1:
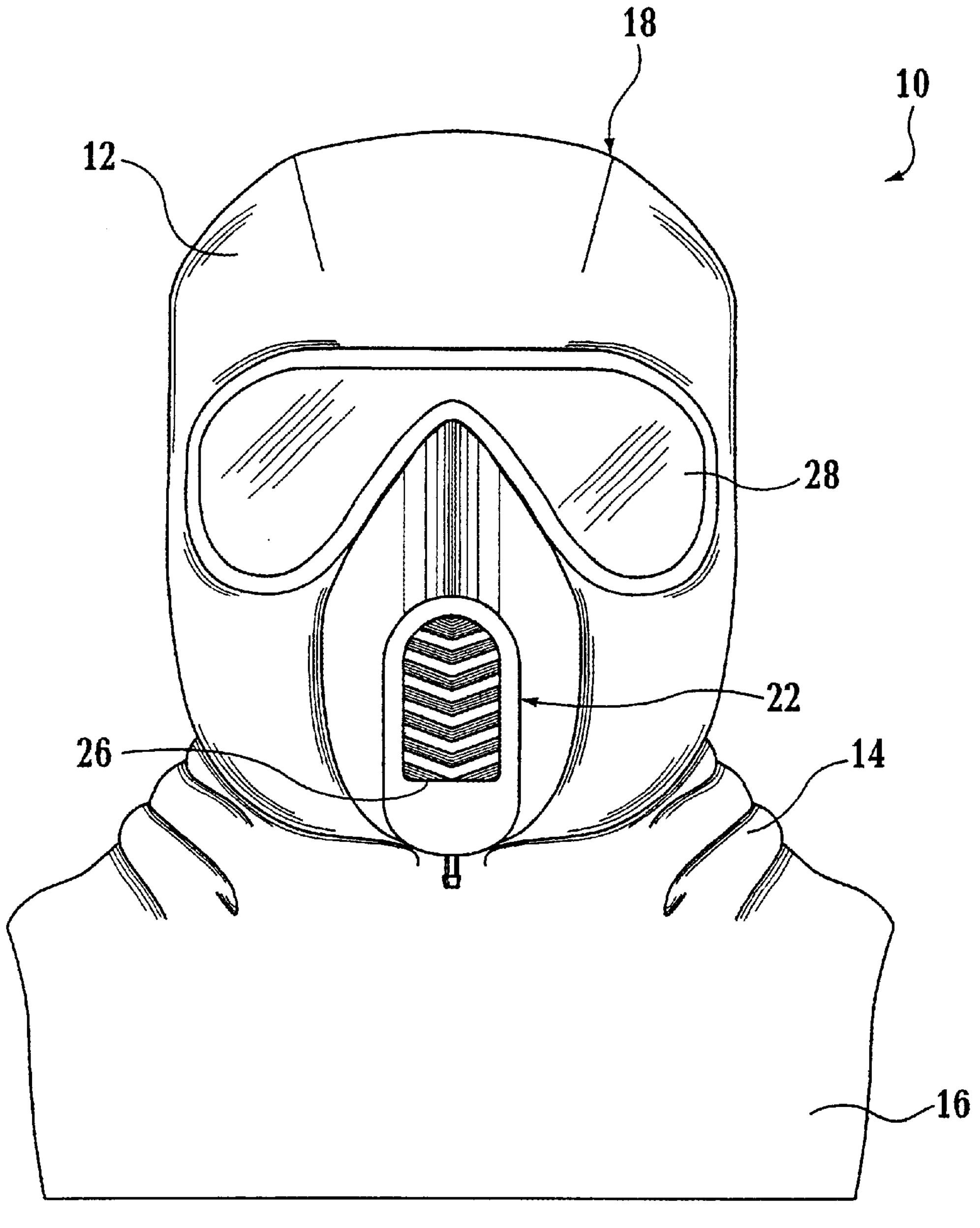
FIG. 1 is a front elevational view of the respiratory mask for one embodiment of the present invention.
Figure 2:
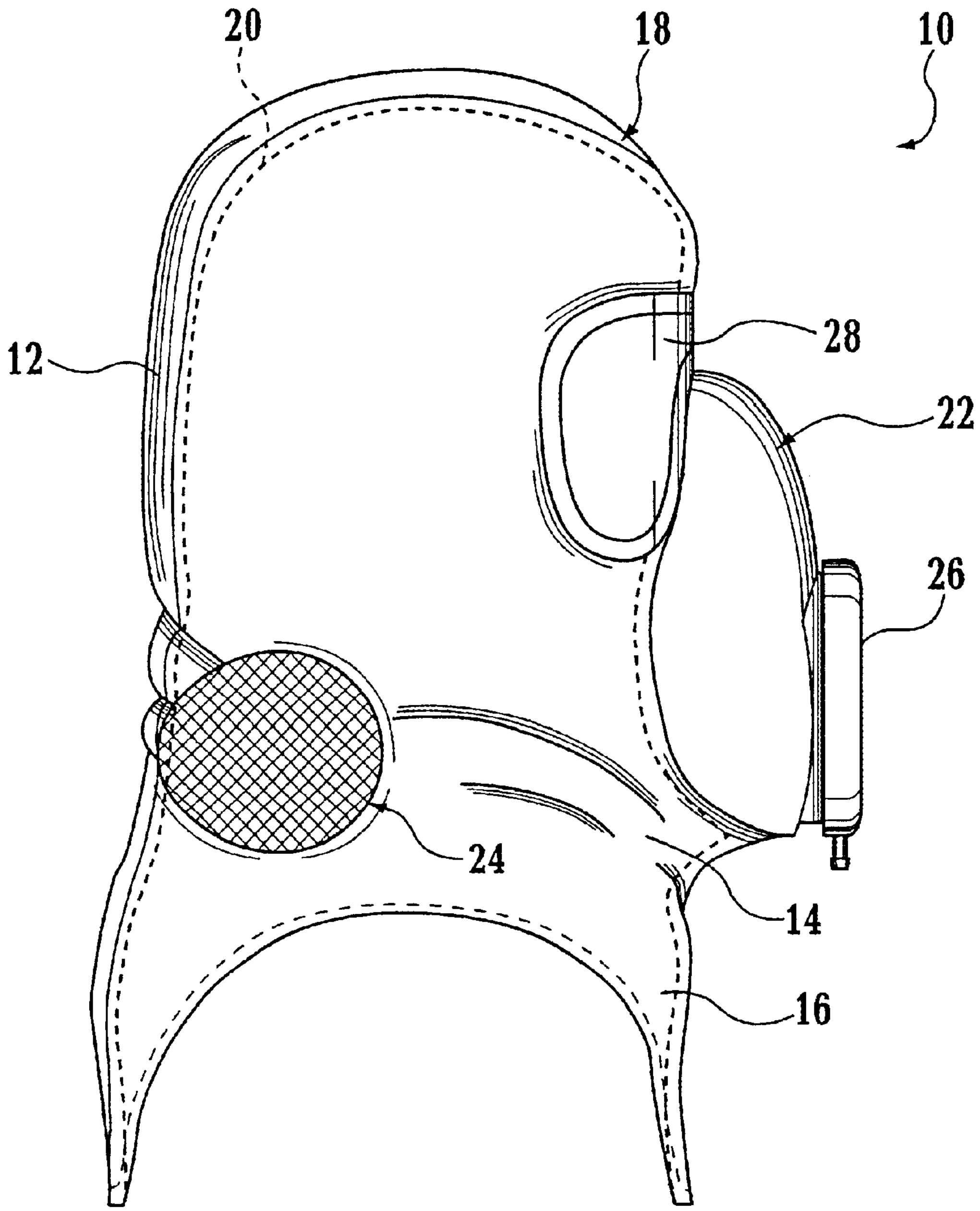
FIG. 2 is a side elevational view of the respiratory mask according to the present invention.

Referring to FIGS. 1 and 2, a respiratory mask assembly 10 of the present invention is shown for one embodiment of the present invention. The respiratory mask assembly or mask 10 comprises generally a head portion 12, a neck portion 14, and a lower portion 16. The mask 10 further includes an outer hood 18, an inner elastic hood 20, a faceplate assembly 22 adapted to fit over a wearer's face and one or more filter assemblies 24 for filtering air drawn into the mask 10. The faceplate assembly 22 further includes an airflow regulator 26 for regulating the flow of air into and out of the wearer's lungs, and a transparent lens piece 28 for providing the user with visual sight through the mask 10. The mask 10 is designed to completely cover and seal the wearer's neck and head from ambient atmosphere.

Figure 3:
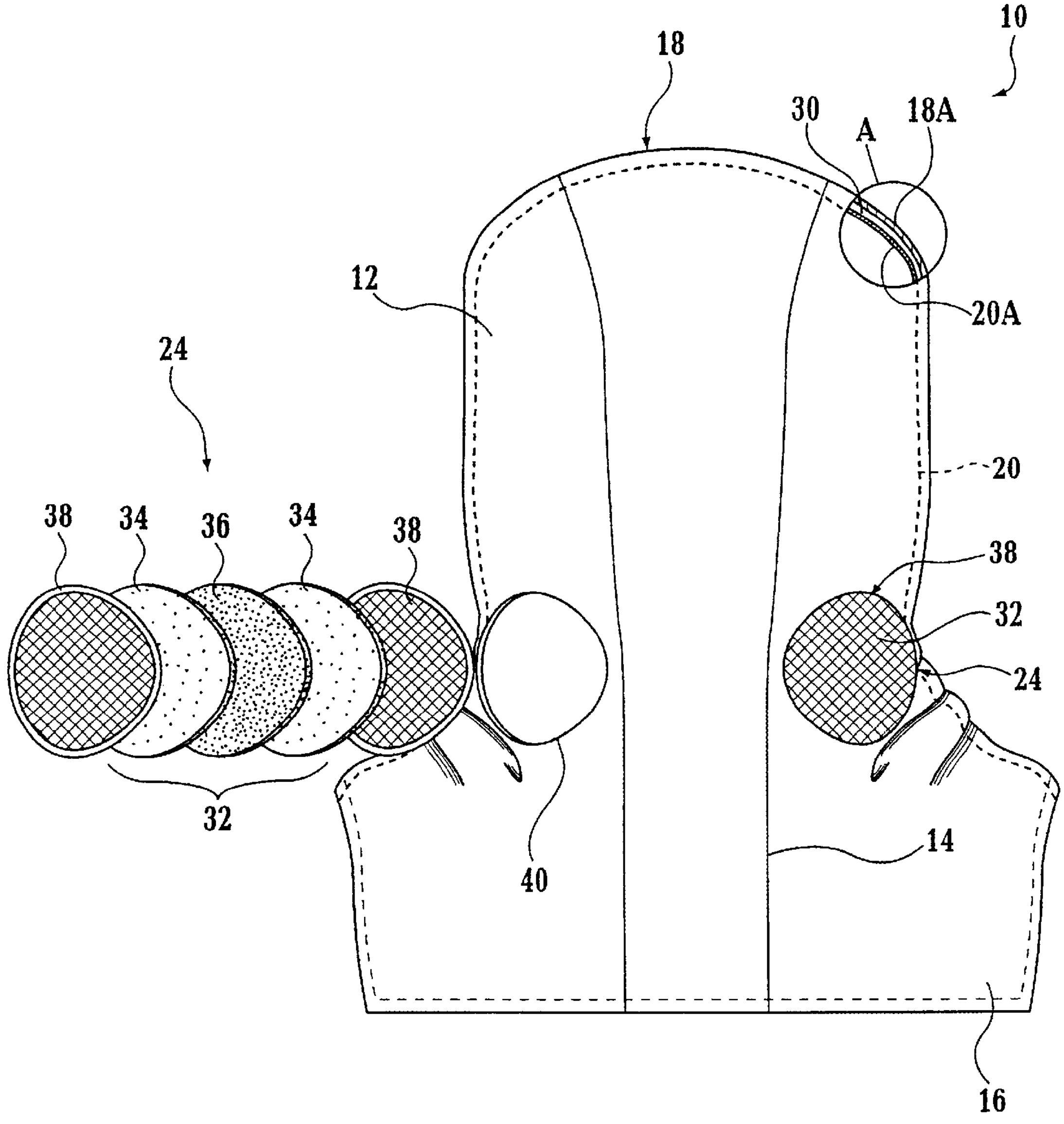
FIG. 3 is a rear elevational view of the respiratory mask according to the present invention.
Figure 4:
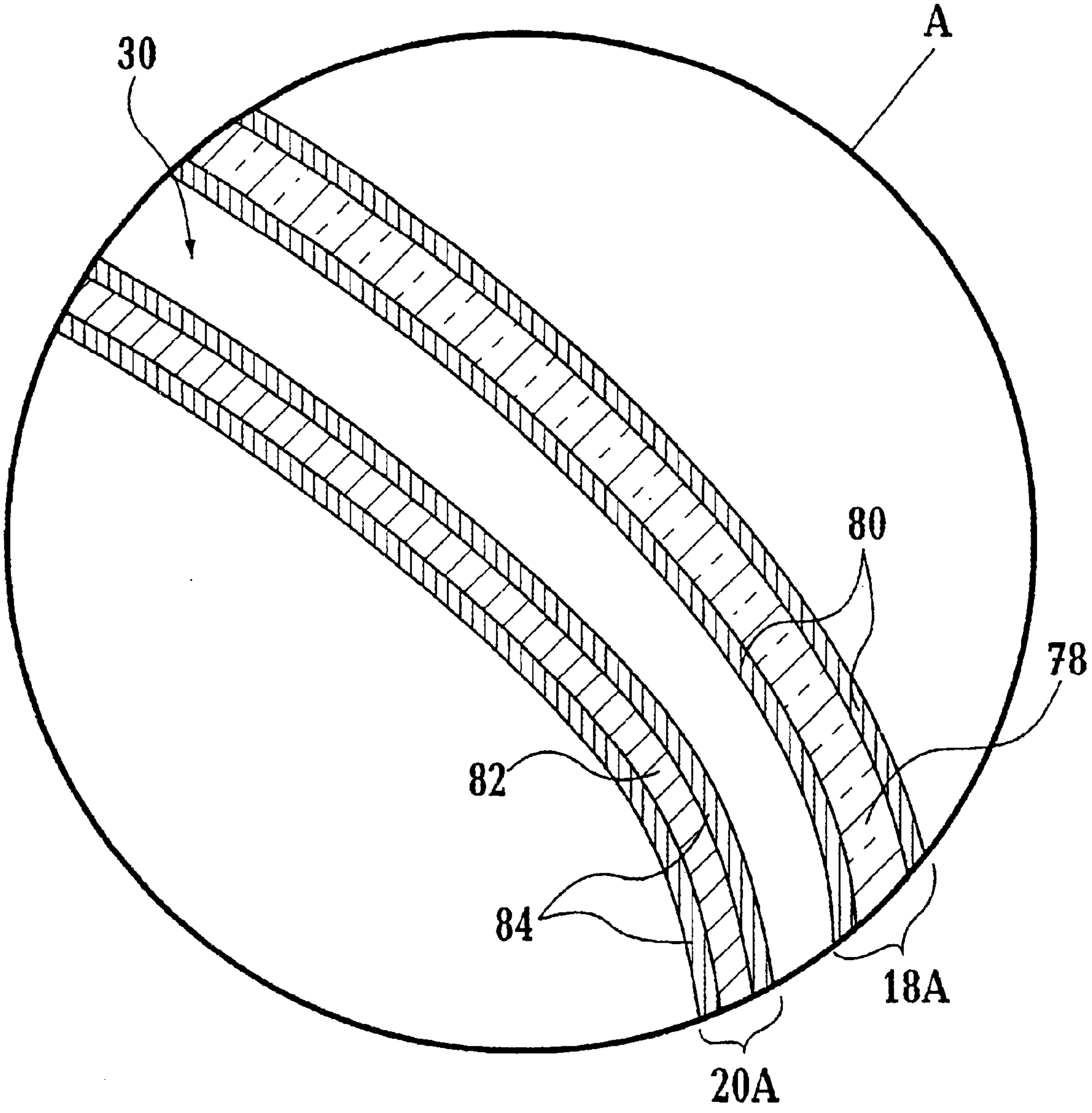
FIG. 4 is an enlarged view of the cross sectional area indicated by "A" in FIG. 3.

With reference to FIG. 3, the outer hood 18 and the inner hood 20 is configured to maintain a spaced-apart arrangement to form a gap space 30 therebetween (see also FIG. 4). The gap space 30 serves as a channel or passage whereby filtered air passing through the filter assemblies 24 is effectively conveyed to the wearer through the airflow regulator 26 of the faceplate assembly 22. The outer and inner hoods 18 and 20 are connected and hermetically sealed along the edge portions thereof to partition the gap space 30 from the ambient atmosphere. Since the wearer breathes the air conveyed through the gap space 30, it is critical to the operation of the mask 10 that the gap space 30 is sealed off from the ambient atmosphere that may contain biologically or chemically hazardous contaminants.

The inner hood 20 is generally composed of a lightweight, breathable fabric material. The fabric material of the inner hood 20 is adapted to allow vapor moisture to pass therethrough from the wearer's skin. The fabric material is stretchable and conforms to the surface of the wearer's head and neck. Optionally, the inner hood 20 may be adapted to prevent penetration of biological or chemical agents for providing additional protection to the wearer.

The outer hood 18 is generally composed of a lightweight, breathable fabric material that is wind-resistant and adapted to allow vapor moisture to pass out to the ambient atmosphere. The fabric material of the outer hood 18 is stiffer and capable of holding its own shape apart from the inner hood 20 to form the gap space 30 therebetween. In addition to its wind resistant and moisture wicking capabilities, the fabric material of the outer hood 18 is further impermeable to airborne aerosol or particulates and liquid water and prevents penetration of hazardous chemical and biological agents into the mask 10.

In an alternative embodiment, the mask 10 may be configured to include a duct or tubing extending between the airflow regulator 26 and filter assemblies 24 in a single layer, outer hood-only arrangement. The duct may include any shape and volume occupying the interior of the mask 10 and conforms substantially along the surface of the wearer's head. The duct may be composed of any suitable material capable of effectively conveying a fluid. In this embodiment, the filtered air passing through the filter assemblies 24 is conveyed through the duct to the airflow regulator 26 of the faceplate assembly 22.

As shown in FIG. 3, the filter assemblies 24 are securely connected to and hermetically sealed along the edges thereof with the outer hood 18. The filter assemblies 24 are fluidly connected to the airflow regulator 26 by the gap space 30. The filter assemblies 24 may be mounted at any location on the mask 10, preferably on the neck portion 14 on the anterior side of the mask 10. Preferably, at least one filter assembly 24 is provided in each mask 10. Each filter assembly 24 includes a multi-laminar filter media 32 that is comprised of a plurality of discrete filter layers securely retained between a pair of mesh screen layers 38. The mesh screen layers 38 are made of thin screen mesh material such as nylon, for example, and are configured to protect the outside and inside surfaces of the filter media 32. The filter media 32 comprises one or more electrostatic, particulate filter layers 34 having a minimum collection efficiency of about 99.97% and one or more carbon activated sorbent layers, or chemical filter layers 36 for absorbing chemical contaminants. Preferably, the filter media 32 possesses low airflow resistance for facilitating comfortable and relatively unlabored breathing, and excellent filtering capacity for protection against hazardous airborne chemicals and biological agents.

The particulate filter layer 34 is generally comprised of a suitable flat-sheet, electrostatically charged, air filtration media (i.e. electrets) that are commercially available. The particulate filter layer 34 is preferably made from an electrostatic media. The electrostatic media material of the particulate filter layer 34 is available from 3M and marketed as ADVANCED ELECTRET MEDIA (AEM). The material offers excellent aerosol filtration and very low pressure drop characteristics. The electrostatic media of the particulate filter layer 34 is optimized to provide near HEPA performance at a thickness of about 0.1 of an inch. The effective surface area of the particulate filter layer 34 may range from about 125 to 300 $cm^2$.

In the preferred embodiment, the chemical filter layer 36 is made from a carbon loaded web. The carbon loaded web material is available from and marketed by 3M. The carbon loading material is commercially available and marketed under CALGON ASZM-TEDA. The carbon loaded web media offers excellent sorbent filtration and low pressure drop characteristics. The web media is preferably loaded to 300 $grams/m^2$ of carbon loading material and layered to provide effective chemical 10 o protection. Preferably, the chemical filter layer 36 comprises four (4) layers of carbon loading material. The effective surface area of the chemical filter layer 36 may range from about 125 to 300 $cm^2$. As shown in FIG. 3, the chemical filter layer 36 is positioned between the particulate filter layers 34. It is noted that the present invention is not limited to the above filtering media and may include the use of any suitable filtration media with low airflow resistance effective for chemical and particulate filtration.

The filter media 32 retained between the pair of mesh screens 38 is mounted in a hood inlet 40 of the outer hood

18. The edge portions of the mesh screens 38, are bonded to the edge of the hood inlet 40 using a suitable sealing element including, but not limited to, adhesives such as silicone adhesives and the like. The thickness of the filter assembly 24 is preferably up to an inch in thickness, and is mounted flush with the outer surface of the outer hood 18 to produce a low profile, contoured fit. The filter media 32 may be compressed stacked in a mold where a thermoplastic edge seal adhesive is injected around the edge portions to form an edge seal. The edge seal sizes are about 0.25 of an inch. The preferred sealant material is a polyurethane-based adhesive such as BJB F60 polyurethane. The preferred sealant material offers fast curing cycles at low temperatures. It is noted that the curing temperature during the edge sealing process should not exceed 150° F. to prevent degradation of the filter media 32. Alternate means of mounting and sealing the filter media 32 onto the outer hood 18 can be used as deemed practical by one skilled in the art.

Referring to FIG. 4, an enlarged view of the cross section of the mask 10 is shown. The outer hood 18 is comprised of an outer hood layer 18A and the inner hood 20 is comprised of an inner hood layer 20A. The gap space 30 formed between the outer and inner hood layers 18A and 20A, provides a pathway for unobstructed fluid flow therethrough. The inner hood layer 20A comprises an elastomeric material layer 82 such as polyurethane bonded on one or both sides with a highly elastic stretch fabric layer 84 such as spandex-like material. It is noted that the inner hood layer 20A may comprise only the fabric layer 84 for increased moisture wicking capacity of the inner hood 20 especially when used in conjunction with a neck seal 74 (see FIG. 6) as will be described herein. In the preferred embodiment, the material of the inner hood layer 20A is an omni-directional stretch fabric available commercially from Darlington Fabrics Corporation (New York, N.Y.) and marketed under the tradename DARLEXX. The preferred material is constructed of three layers. The middle layer is a hydrophilic, thermoplastic, urethane film that is bonded on each side to a layer of stretchable fabric containing approximately 80% nylon and 20% spandex elastomer. The film effectively prevents the penetration of particulate contaminants and yet is “breathable” in the sense that it allows for moisture-vapor transmission from the wearer’s skin. The film also serves as an effective barrier against wind and water. Other laminated breathable fabrics, such as those made from GORE-TEX materials from W. L. Gore & Associates, Inc. (Elkton, Md.), are also useful for the construction of the inner hood 20.

One particular main advantage of DARLEXX fabric is its unique combination of elasticity coupled with waterproof-breathable stretch that allows the inner hood 20 to be form fitting, thereby increasing the fit and comfort of the mask 10. The ability of the fabric to transport water vapor significantly reduces thermal stress caused by heat and moisture build up. This is a problem found especially in hood respirators made of rubber (e.g., latex, silicone, butyl rubber, etc.) and other impermeable (non-breathable) materials.

The material of the outer hood layer 18A is preferably comprised of a fabric material layer 78 preferably GORE-TEX materials from W. L. Gore & Associates, Inc. (Elkton, Md.), with a stable, chemically resistant thermoplastic polymer layer film 80 such as SARANEX, EVOH, and TEFLON, preferably TEFLON, laminated on one or both sides of the fabric material layer 78. The preferred GORE-TEX material is available as selectively permeable membranes designated as CHEMPAK or impermeable films designated as HSF. The materials provide excellent chemical resistance in very thin laminated structures. Preferably the thickness of the TEFLON film layer 80 is about 0.00001 to 0.01 of an inch, more preferably about 0.0001 of an inch. Alternatively, the fabric material layer 78 may comprise other materials including, but not limited to, nylon, polyester, and NOMEX. The layer film 80 may comprise other materials including, but not limited to, latex, organic rubbers, and thermoplastic polymers.

As illustrated in FIGS. 1 through 3, two seams preferably run along the top of the mask 10 in each hood 18 or 20 to form a conformal shape. As may be apparent to one skilled in the art, other hood seam patterns may be used to produce a form fit with the wearer’s head. Each fabric is sewn and the inside taped using a suitable adhesive to produce an effective seal. Alternatively, the fabric seams may be sewn and heat taped or bonded with an appropriate adhesive or sealant. All the components would be typically bonded with a silicone type adhesive or a hot melt adhesive, although any suitable adhesive may be used.

Figure 5:
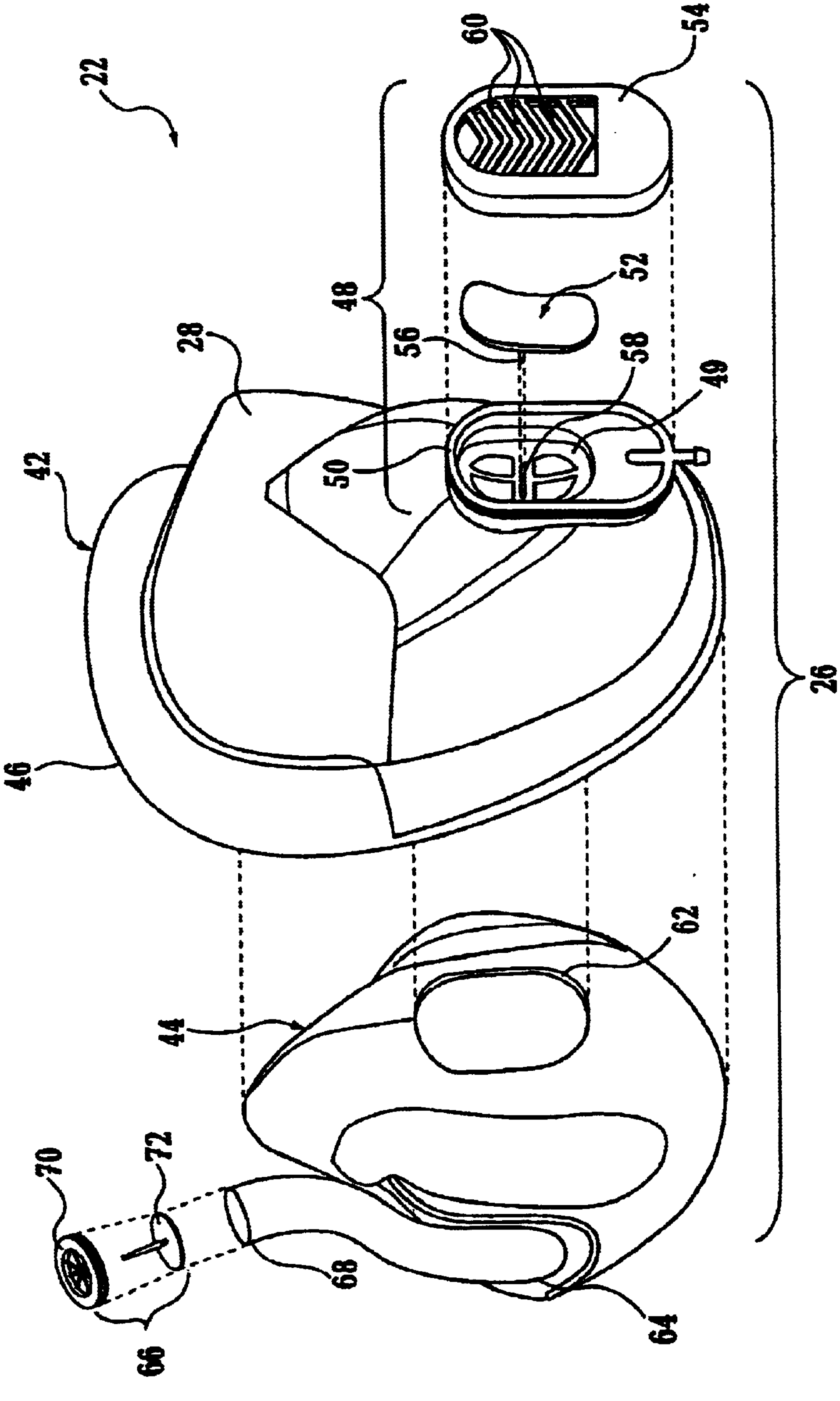
FIG. 5 is an exploded assembly view of a faceplate assembly of the respiratory mask according to the present invention.

Referring to FIG. 5, an integral faceplate assembly 22 is provided that is sized and shaped to fit the wearer’s face. The faceplate assembly 22 comprises a flexible faceplate element 42, a clear, transparent lens piece 28, and a nose cup member 44 wherein the nosecup member 44 and the flexible faceplate element 42 in combination forms the airflow regulator 26. The lens piece 28 is dimensioned and shaped to allow a wide horizontal and lateral field of view, The lens piece 28 is comprised of a clear, thin, flexible, plastic material. The preferred lens material is cast-formed polyurethane that has excellent optical properties, durability, and flexibility. Other suitable materials include clear thermoplastic polyvinyl chloride that can also be used to form the lens piece 28. The lens piece 28 is attached to the faceplate element 42 through suitable means including adhesives, sealant, and the like.

The faceplate element 42 includes a flange portion 46 extending substantially therearound, and a centrally located outlet valve unit 48. The outer hood 18 and the inner hood 20 is each provided with an opening for the mounting of the faceplate assembly 22. The edge portion of the outer hood opening is bonded or insert molded to the faceplate flange portion 46 in sealing engagement leaving the lens piece 28 and the outlet valve unit 48 exposed to ambient. The inside edge portion of the faceplate element 42 is attached to the outer edge portion of the inner hood opening through suitable means whereby means are provided to preserve and maintain the fluid communication between the interior side of the faceplate assembly 22 and the gap space 30. Alternatively, the outer edge portion of the inner hood opening may remain unattached to the faceplate element 42 and overlays on the wearer’s head. In the latter, means are provided to ensure the faceplate element 42 and the nose cup member 44 remain pressed against the wearer’s face during use. The faceplate element 42 is preferably molded from an elastic elastomer material such as silicone rubber, polyurethane, thermoplastic elastomers, and the like. The preferred material is cast polyurethane marketed as SIM 10 from Simula Technologies (Phoenix, Ariz.). The thickness of the faceplate element 42 may range from about 0.04 to 0.08 of an inch, preferably 0.060 of an inch, The nose cup 44 may be integrally molded into faceplate element 42 or provided as a separate piece as shown in FIG. 5.

The airflow regulator 26 of the faceplate assembly 22 provides proper respiratory airflow management and lens piece defogging In the preferred embodiment, the airflow regulator 26 comprises the nose cup 44 which can be made of silicone rubber, latex, or organic rubber, or other suitable elastomer that is hypoallergenic and provides a comfortable flexible seal along the skin surface around the wearer’s nose and mouth. One preferred material is the DOW CORNING RTV-S silicone rubber material The material offers excellent flexibility and environmental stability for folded stowage of the mask 10. The nose cup 44 is adapted to fit a large range of face sizes and shapes. The nose cup 44 is designed with a contoured sealing flange and extended side flanges to provide a comfortable and effective seal. The thickness of the nose cup 44 is typically in the range of from about 0.030 to 0.080 of an inch, preferably about 0.060 of an inch.

The airflow regulator 26 includes the centrally located outlet valve unit 48 in the faceplate element 42 for releasing exhaled air, and an inlet valve unit 66 in the nose cup 44 positioned near the bridge of the nose for drawing fresh filtered air from the gap space 30. The outlet valve unit 48 has an opening 49, a seat portion 50, a rubber flapper valve 52, and a protective cover 54. The flapper valve 52 includes a tab 56 which is inserted into a slot 58 for secure mounting with the seat portion 50. The protective cover 54 includes a plurality of vents 60 and is adapted for snug retainment over the seat portion 50. The nose cup 44 has an exhalation opening 62 that is connected to and in communication with the internal side of the valve unit 48. The valve unit 48 opens to permit carbon dioxide ($CO_2$) and moisture to exit from the nose cup 44 during exhalation. The flapper valve 52 permits air to flow outwardly under positive pressure, however, under negative pressure, the flapper 52 retracts to block the opening 49 and prevent entry of air into the mask 10. Alternate low-resistance commercially available exhalation valve assemblies having a size and shape compatible with the faceplate element 42 and mask design can also be used.

The nose cup 44 further includes a snorkel member 64 with an inlet opening 68 at which the inlet valve unit 66 is attached thereto. The snorkel member 64 positions the inlet opening 68 near the bottom edge of the lens piece 28. In this configuration, the inhaled air sweeps across the surface of the lens piece 28 to maintain a relatively condensation free condition on the lens. The inlet valve unit 66 used in the present invention can be of the same types used in any of the conventionally available chemical/biological protective masks. Preferably, the inlet valve unit 66 includes a plastic seat 70 and a thin rubber flapper valve 72. The inlet valve unit 66 opens during inhalation and closes during exhalation to prevent $CO_2$, moisture and heat buildup under the mask 10. The airflow regulator 26 is provided to allow exhaled air to escape while preventing inward leakage of contaminants during inhalation. This feature, along with the use of a contoured tight fitting nose cup 44, prevents $CO_2$ build up by substantially reducing the respiratory dead air space inside the mask 10.

Figure 6:
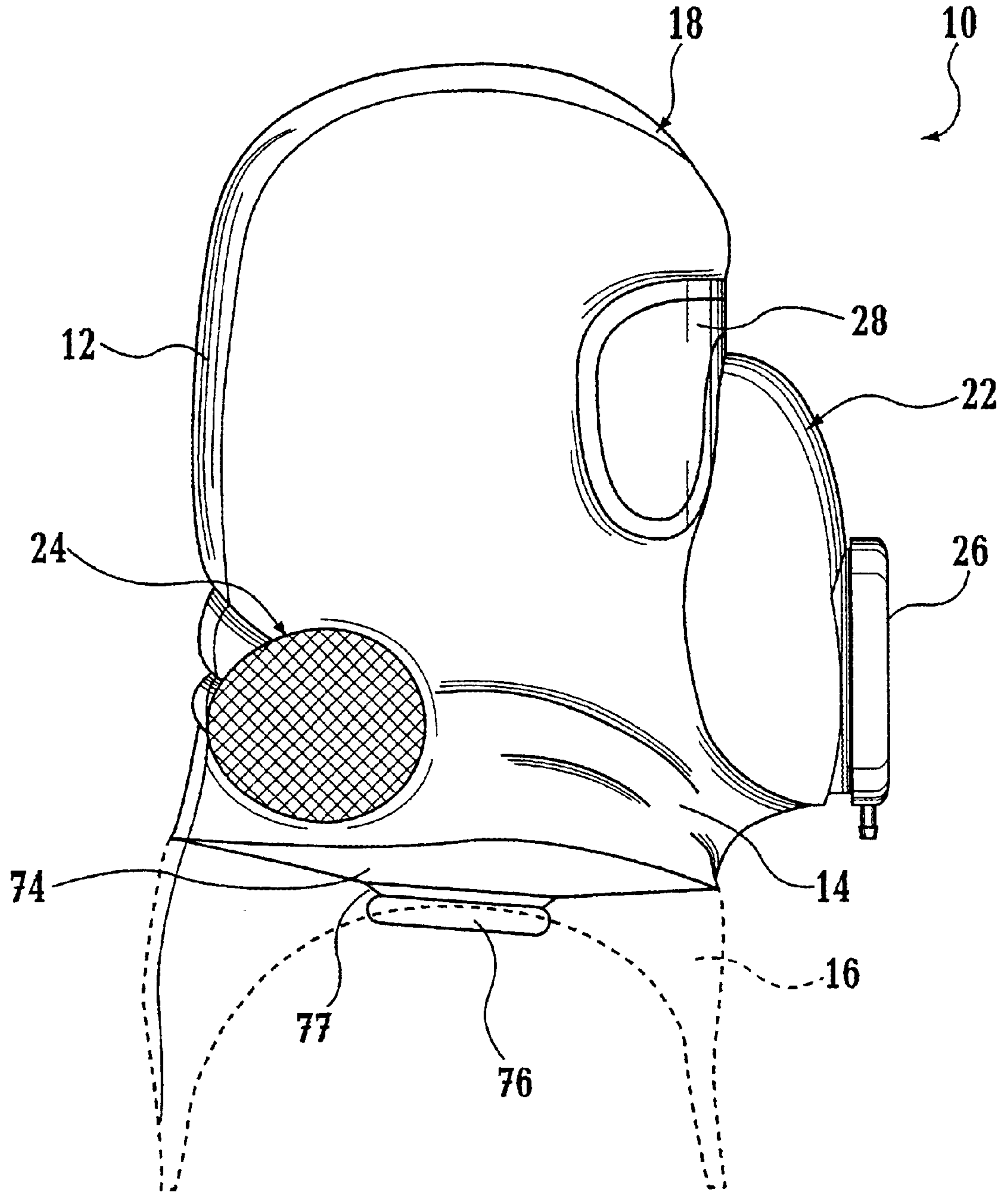
FIG. 6 is a side elevational view of the respiratory mask partially in phantom showing a neck seal component located inside thereof according to the present invention.

The contour fit of the nose cup 44 and the inner hood 20 provides the wearer with a primary sealing interface with the mask 10. As shown in FIG. 6, the mask 10 includes a neck seal 74 that provides an additional sealing interface for the mask 10. The neck seal 74 is adapted to provide sealing protection for a range of neck sizes. The neck seal 74 is molded to form a tapered opening 76 that is designed to maximize skin contact and fit snugly around the neck to ensure a leak proof seal. The opening includes a flange portion 77 extending along the periphery of the opening 76 for providing additional sealing contact with the skin around the neck. As noted above, the inner hood 20 may be comprised of a non-laminated fabric material layer as used in conjunction with the neck seal 74. It is preferable for the inner hood 20 to be comprised of the laminated structure shown in FIG. 4 for improved chemical/biological protection.

The overall diameter of the neck seal 74 may range from about 8 to 15 inches, preferably about 11 inches. The opening 76 is die cut or molded to prevent tearing when the hood is donned. The opening 76 includes an opening diameter of from about 2 to 3.25 inches, preferably about 2.75 inches. The thickness of the neck seal 74 may range from about 0.01 to 0.030 of an inch, preferably 0.025 of an inch. The neck seal 74 is designed to fit at least 99% of the adult male and female population. Alternative neck seal 74 opening sizes and thickness could be evaluated for optimum fit, seal and comfort, and used in the design as deemed necessary by one skilled in the art. Alternatively, the neck seal 74 may be mounted to the lower portion 16 of the mask 10 for sealing the mask 10 from ambient.

The neck seal 74 is preferably composed of a thin sheet of silicone rubber, latex, organic rubber or a suitable elastomer material. Silicone rubber is preferable since it is comfortable, highly elastic, and hypoallergenic. The invention preferably uses a silicone rubber material marketed under DOW CORNING RTV-S, since it has been found to have adequate strength, environmental stability, and excellent flexibility and elongation to avoid being torn when stretched over the head and donned.

Although various embodiments of the invention have been shown and described, they are not meant to be limiting. Those of skill in the art may recognize various modifications to these embodiments, which modifications are meant to be covered by the spirit and scope of the appended claims.

What is claimed is:

1. A respiratory mask assembly for filtering airborne biological and/or chemical agents from air for breathing, said assembly comprising:

an outer hood adapted to seal with and encompass at least the head and neck of a wearer from ambient atmosphere;

at least one transparent lens attached to said outer hood for providing visual sight to the wearer;

at least one filter assembly attached to said outer hood, said filter assembly adapted for filtering airborne biological and/or chemical agents from air passing therethrough;

an airflow regulator located in said outer hood, said airflow regulator including an outlet adapted for expelling exhaled air to ambient, and an inlet adapted for drawing air thereinto;

an inner elastic hood located inside said outer hood and adapted for conforming to the contours of at least the head and neck of the wearer; and a gap space defined between said outer and inner hoods and sealed from ambient air, said gap space providing a means for channeling air drawn from ambient air and filtered through said filter assembly across said transparent lens and into said airflow regulator inlet.

2. The mask assembly of claim 1, wherein said at least one filter assembly comprises a filter media.

3. The mask assembly of claim 2, wherein said filter media comprises:

at least one chemical filter layer including a web media loaded with a sorbent carbon substrate adapted for filtering chemical agents; and at least one particulate layer including an electrostatic media adapted for filtering particulates and aerosols.

4. The mask assembly of claim 1, further comprising a neck seal attached to and extending circumferentially along a lower edge portion of said inner hood.

5. The mask assembly of claim 4, wherein said neck seal is comprised of an elastic material.

6. The mask assembly of claim 4, wherein said neck seal is comprised of silicone rubber.

7. The mask assembly of claim 2, further comprising a pair of filter assemblies located at an anterior portion of said outer hood.

8. The mask assembly of claim 2, wherein said airflow regulator includes a nose cup assembly.

9. The mask assembly of claim 8, wherein said nose cup assembly comprises a centrally located outlet valve assembly and an inlet valve assembly connected to an inlet thereof located near said transparent lens for directing air drawn from said gap space to sweep across the surface of said transparent lens.

10. The mask assembly of claim 1, wherein said transparent lens comprises a cast-formed polyurethane material.

11. The mask assembly of claim 1, wherein said outer hood comprises an chemical resistant material layer bonded on at least one side with a fabric layer, and wherein said outer hood is adapted for transmitting heat and moisture vapor generated by said wearer, and preventing transmission of particulates and liquids therethrough.

12. The mask assembly of claim 11, wherein said fabric material layer comprises a material selected from the group consisting of nylon, polyester, and NOMEX.

13. The mask assembly of claim 11, wherein said chemical resistant material layer comprises a material selected from the group consisting of GORE-TEX, CHEMPAK, and HSF.

14. The mask assembly of claim 11, wherein said fabric material layer further comprises a stable, chemically resistant film laminated thereto.

15. The mask assembly of claim 14, wherein said stable, chemically resistant film is thermoplastic.

16. The mask assembly of claim 15, wherein said stable, chemically resistant thermoplastic film is selected from the group consisting of TEFLON, SARANEX, and EVOH.

17. The mask assembly of claim 1, wherein said inner hood comprises an elastomeric material layer bonded on at least one side with a highly elastic stretch fabric layer, wherein said inner hood is adapted for transmitting heat and moisture vapor generated by said wearer.

18. The mask assembly of claim 17, wherein said inner hood comprises DARLEXX.

19. The mask assembly of claim 17, wherein said highly elastic stretch fabric layer is further adapted for preventing transmission of particulates and liquids.

20. The mask assembly of claim 17, wherein: said highly elastic stretch fabric layer comprises 80% nylon and 20% spandex; and said elastomeric material layer comprises a thermoplastic polymer.

21. The mask assembly of claim 17, wherein said elastomeric layer is polyurethane.

* * * * *